(12) United States Patent
Künecke et al.

(10) Patent No.: US 10,017,102 B2
(45) Date of Patent: Jul. 10, 2018

(54) LIGHTING DEVICE WITH PRIMARY LIGHT SOURCE AND PHOSPHOR VOLUME WITH AN EVALUATION UNIT

(71) Applicant: OSRAM GmbH, Munich (DE)

(72) Inventors: Jan-Erik Künecke, Regensburg (DE); Georg Forster, Regensburg (DE)

(73) Assignee: OSRAM GMBH, Munich (DE)

( * ) Notice: Subject to any disclaimer, the term of this patent is extended or adjusted under 35 U.S.C. 154(b) by 35 days.

(21) Appl. No.: 15/118,496

(22) PCT Filed: Feb. 4, 2015

(86) PCT No.: PCT/EP2015/052286
§ 371 (c)(1),
(2) Date: Aug. 12, 2016

(87) PCT Pub. No.: WO2015/124428
PCT Pub. Date: Aug. 27, 2015

(65) Prior Publication Data
US 2017/0240094 A1    Aug. 24, 2017

(30) Foreign Application Priority Data
Feb. 18, 2014   (DE) .................. 10 2014 202 943

(51) Int. Cl.
*B60Q 1/04*      (2006.01)
*B60Q 1/00*      (2006.01)
(Continued)

(52) U.S. Cl.
CPC ............. *B60Q 1/0023* (2013.01); *B60Q 1/04* (2013.01); *F21S 48/1145* (2013.01);
(Continued)

(58) Field of Classification Search
CPC .......... B60Q 1/04; G01J 1/4257; F21S 48/13; G01N 21/95; G02B 6/0003
(Continued)

(56) References Cited

U.S. PATENT DOCUMENTS

| 4,727,252 A * | 2/1988 | Yoshimura ............ G01T 1/2016 250/588 |
| 2011/0063115 A1 | 3/2011 | Kishimoto |

(Continued)

FOREIGN PATENT DOCUMENTS

| JP | 2013191479 A | 9/2013 |
| WO | 2013096984 A1 | 7/2013 |

(Continued)

OTHER PUBLICATIONS

International Search Report based on Application No. PCT/EP20151052286 (4 Pages and 3 Pages of English translation) dated May 12, 2015 (Reference Purpose Only).

*Primary Examiner* — Que T Le
(74) *Attorney, Agent, or Firm* — Viering Jentschura & Partner MBB

(57) ABSTRACT

Various embodiments may relate to a lighting device, including at least one primary light source for generating primary light, a phosphor volume spaced apart from the at least one primary light source and serving for at least partly converting the primary light into secondary light having a different wavelength, at least one light sensor for detecting light generated by the at least one primary light source, and an evaluation unit for determining a case of damage of the phosphor volume on the basis of sensor data of at least one light sensor. The lighting device includes at least one additional light source for irradiating the phosphor volume, and is designed to operate the at least one additional light source, (Continued)

the at least one light sensor and the evaluation unit with the primary light source switched off.

10 Claims, 1 Drawing Sheet

(51) Int. Cl.
*F21S 8/10* (2006.01)
*G01N 21/95* (2006.01)
*G01J 1/42* (2006.01)

(52) U.S. Cl.
CPC ........... *F21S 48/1225* (2013.01); *F21S 48/13* (2013.01); *G01J 1/4257* (2013.01); *G01N 21/95* (2013.01); *G01N 2201/06113* (2013.01)

(58) Field of Classification Search
USPC .................................. 250/205, 214 R, 214.1
See application file for complete search history.

(56) References Cited

U.S. PATENT DOCUMENTS

| | | |
|---|---|---|
| 2011/0116520 A1 | 5/2011 | Krijn et al. |
| 2014/0334167 A1 | 11/2014 | Tiefenbacher |
| 2015/0043233 A1 | 2/2015 | Bauer et al. |

FOREIGN PATENT DOCUMENTS

| | | |
|---|---|---|
| WO | 2013134807 A1 | 9/2013 |
| WO | 2014072226 A1 | 5/2014 |

* cited by examiner

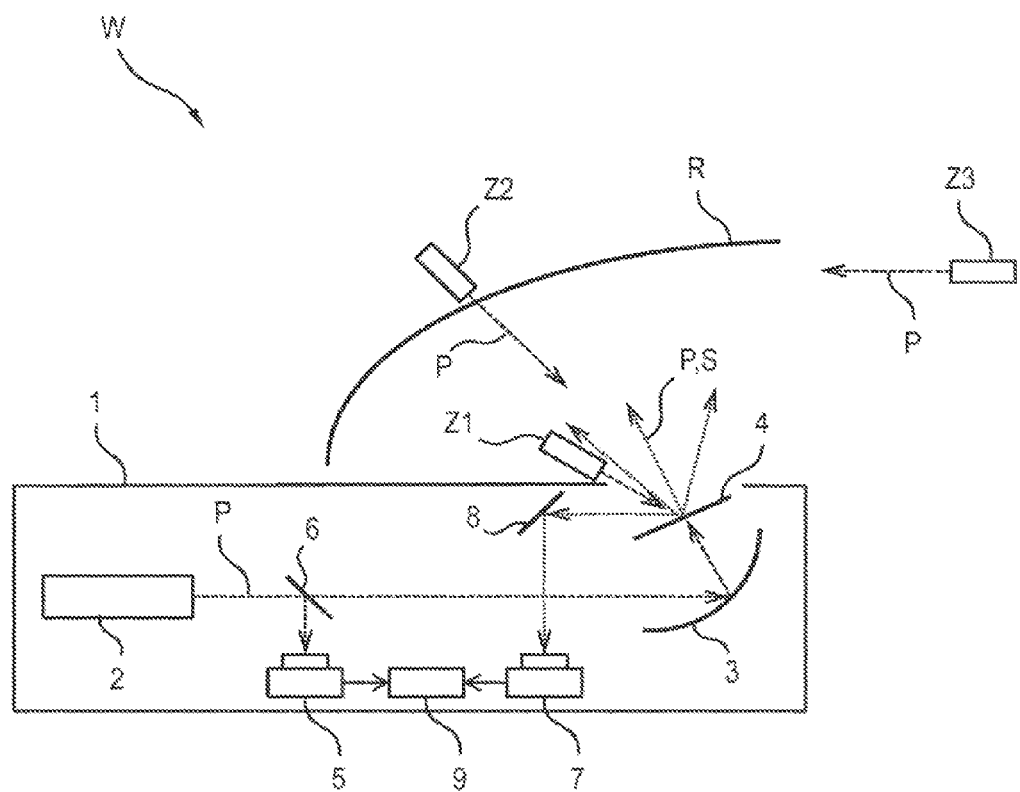

LIGHTING DEVICE WITH PRIMARY LIGHT SOURCE AND PHOSPHOR VOLUME WITH AN EVALUATION UNIT

RELATED APPLICATIONS

The present application is a national stage entry according to 35 U.S.C. § 371 of PCT application No.: PCT/EP2015/052286 filed on Feb. 4, 2015, which claims priority from German application No.: 10 2014 202 943.0 filed on Feb. 18, 2014, and is incorporated herein by reference in its entirety.

TECHNICAL FIELD

Various embodiments may relate to a lighting device, including at least one primary light source for generating primary light, a phosphor volume spaced apart from the at least one primary light source and serving for at least partly converting the primary light into secondary light having a different wavelength, at least one light sensor for detecting light generated by means of the at least one primary light source, and an evaluation unit for determining a case of damage of the phosphor volume on the basis of sensor data of at least one light sensor. Various embodiments also relate to a method for determining a case of damage of a phosphor volume of a lighting device. Various embodiments are applicable in particular to the field of vehicle lighting systems, in particular exterior lighting, e.g. for generating an additional light, a daytime running light, etc. Various embodiments are applicable in particular to headlights, for example for trucks, automobiles or motor cycles.

BACKGROUND

Lighting devices are known in which primary light is partly converted into secondary light having a longer wavelength by means of a phosphor. In this case, the phosphor is arranged remote from the primary light source, which is also referred to as "remote phosphor". The phosphor then emits a mixed light having a portion of non-converted or unconverted primary light and a portion of the secondary light as useful light. In the case of blue primary light, blue-yellow-converting phosphor and hence yellow secondary light, a blue-yellow or white mixed light may be generated. If the phosphor volume is damaged (e.g. owing to the occurrence of cracks and/or holes in the phosphor volume), the primary light can radiate through the phosphor volume undesirably to an intense degree. The lighting device may then emit primary light having a high intensity, which brings about undesired lighting effects or can even cause damage to health, e.g. eye damage from direct viewing of the lighting device. This disadvantage is particularly pronounced when a laser is used as primary light source.

It is known to use a light sensor in order to detect an intensity of the mixed light generated by means of the primary light source and thereby to determine a case of damage of the phosphor volume on the basis of sensor data of said light sensor by means of an evaluation unit. What is disadvantageous here is that, when there is a case of damage, within the period of time that elapses until the case of damage has been recognized, the intensive primary radiation can emerge from the lighting device.

SUMMARY

The object of the present disclosure is at least partly to overcome the disadvantages of the related art and in particular to enable an improved safety with regard to emergence of relatively intensive primary radiation when there is a case of damage of the phosphor volume, in particular an improved eye safety.

Various embodiments provide a lighting device, including at least one primary light source for generating primary light, a phosphor volume spaced apart from the at least one primary light source and serving for at least partly converting the primary light into secondary light having a different wavelength, at least one light sensor for detecting light generated by the at least one primary light source, and an evaluation unit for determining a case of damage of the phosphor volume on the basis of sensor data of at least one light sensor, wherein the lighting device includes at least one test or additional light source for irradiating the phosphor volume and is designed to operate the at least one additional light source, the at least one light sensor and the evaluation unit with the primary light source switched off.

This achieves the advantage that mechanical damage of the phosphor volume as a result of holes and/or cracks can be recognized before the lighting device undergoes transition to a normal operating mode with activation of the primary light source(s). In other words, the activation of the primary light source(s) can be preceded by a test phase in which primary light radiation does not emerge or does not emerge to a harmful extent. If the test phase reveals that damage of the phosphor volume is present, a warning may be issued or normal operation may even be prevented.

The at least one primary light source may include for example at least one light emitting diode (LED) and/or at least one laser. The at least one primary light source may include in particular at least one semiconductor light source, wherein a laser can be embodied for example as a laser diode.

The primary light may be e.g. UV light or blue light, which have a short wavelength and are thus suitable for activating a particularly large number of phosphors.

The phosphor volume may include one or more phosphors. At least one of the phosphors (if appropriate the sole phosphor) commits the primary light into secondary light, e.g. blue primary light into yellow secondary light. If a plurality of phosphors are present, at least one of the phosphors may convert previously converted secondary light further into secondary light having an even longer wavelength (also referred to as "tertiary light"). By way of example, in the case of UV light as the primary light, two phosphors may convert the UV light into blue and green secondary light and a third phosphor may convert part of the green secondary light into red secondary light.

The phosphor volume may be used in a transmitted-light construction or transmissive construction in which wavelength-converted light and primary light that passed through the phosphor volume, if appropriate, can be tapped off as useful light at a side (the "useful light side") of the phosphor volume which faces away from a side on which the primary light is incident. The phosphor volume may also be used in a reflective construction in which wavelength-converted secondary light and, if appropriate, non-converted primary light can be tapped off at a side (the useful light side) of the conversion unit onto which the primary light can also be radiated.

The useful light side of the phosphor volume can thus be understood to mean, in particular, that side of the phosphor volume from which the useful light that is used further is emitted.

The phosphor volume may be present in particular as a layer, that is to say have a height which is significantly smaller than an extent in a plane perpendicular thereto. The phosphor volume may be present for example as a lamina or as a disk.

The phosphor volume may be applied on a carrier. The carrier may consist of light-transmissive material, in particular of transparent material, for the case of a transmitted-light construction (transmissive construction). The carrier may be e.g. a sapphire lamina. For the case of a reflective construction, the carrier may have a diffusely or specularly reflective surface facing the phosphor volume. It may then consist of metal e.g. for effective cooling.

The conversion of the primary light into secondary light may take place only partly e.g. if the non-converted part of the primary light is intended to be used as a useful light portion, e.g. as a blue light portion in a blue-yellow mixed light. However, the conversion of the primary light into secondary light may also be complete, e.g. if the primary light is UV light.

The at least one light sensor may include in particular at least one brightness sensor. The latter may in particular be able to detect a measure of a brightness of the light incident on it and to output that as sensor data. At least one light sensor may additionally be spectrally sensitive, that is to say that it is sensitive only to light in a predetermined spectral range, e.g. only to the primary light or only to a secondary light.

The light generated by means of the at least one primary light source may include the primary light generated directly by the at least one primary light source and/or the at least one secondary light generated indirectly thereby by the phosphor volume. The at least one light sensor may thus be sensitive in particular to the primary light and/or to at least one secondary light and/or to at least one tertiary light.

The evaluation unit may be e.g. a logic or electronic unit which is coupled to the at least one light sensor and thus receives the sensor data thereof.

The at least one light sensor may be a light sensor specifically provided for testing the phosphor volume. It is advantageous for saving costs if the at least one light sensor is also used when the primary light source is activated or during normal operation, e.g. for controlling or regulating a luminous flux and/or for ascertaining damage during normal operation. The lighting device can thus also be configured to recognize a case of damage during normal operation. The recognition of damage in the test phase and during normal operation may be based here on different or identical methods.

The at least one additional light source is a light source different than the at least one primary light source. This enables a different arrangement, in particular beam direction, a simplified driving and also a flexible configuration of the additional light source. By using the at least one additional light source, the at least one light sensor and the evaluation unit it is possible to carry out the test phase even with the primary light source switched off.

In one development, the at least one additional light source emits light having a lower intensity than the at least one primary light source. As a result, even for the case where mechanical damage of the phosphor volume is present, the intensity can be kept below a damaging threshold. A number of additional light sources smaller than the number of primary light sources may be used for this purpose. Alternatively or additionally, at least one additional light source emits light having a lower intensity than at least one primary light source.

In one configuration, the at least one additional light source is configured to radiate its light onto a useful light side of the phosphor volume. Consequently, its light, at least in the case of a transmitted-light construction, will be incident on the phosphor volume in a direction which is opposite to a direction of the light emitted by the phosphor volume during normal operation. This configuration has the advantage that here in the test phase practically no light of damaging intensity emerges from the lighting device.

The additional light source may be a laser. The additional light source may be a semiconductor light source, e.g. an LED, an OLED, or a laser diode. However, the additional light source is not restricted thereto. An additional light source may correspond to a primary light source in terms of its type or may be embodied differently than a primary light source. The additional light source is however not restricted to semiconductor light sources and may e.g. also be a halogen incandescent lamp, a dielectric barrier discharge light source, an infrared light source, an electron beam source, a microwave source (resonator), etc.

In another configuration, at least one light sensor is configured and arranged to detect light emitted by the phosphor volume. This can make use for example of the fact that a light emission pattern of a phosphor volume provided with cracks and/or holes differs from a light emission pattern of an undamaged phosphor volume, since cracks and holes alter the reflection behavior of the light (of the primary light and/or of the at least one secondary light), in particular bring about a dependence or amplified dependence of the intensity on a solid angle (direction dependence). Consequently, a presence of cracks and/or holes can be ascertained by a change in a light intensity received at a light sensor, wherein the light sensor detects in particular light emitted into a predetermined solid angle.

In a further configuration, a plurality of light sensors are arranged in the circumferential direction around the phosphor volume, in particular in a manner spaced apart uniformly. As a result, the solid-angle- or direction-dependent change in the light emission pattern can be ascertained particularly reliably. In this regard, the change in intensity may be able to be ascertained more easily by a common or correlated consideration of sensor data of a plurality of light sensors. Moreover, the change in intensity nay be able to be ascertained more easily if it can be clearly ascertained only in a limited solid angle range. This configuration includes the fact that the light sensors themselves are arranged in the circumferential direction around the phosphor volume or that tapping units (e.g. beam splitters, deflection mirrors, light entrance surfaces of an optical waveguide, etc.) are arranged in this way. The tapping units guide at least part of the light incident on them to at least one associated light sensor, wherein the light sensors then need not be arranged in the circumferential direction around the phosphor volume. A possible arrangement diversity is thus increased.

In one development, a plurality of light sensors are arranged in the circumferential direction around the phosphor volume, which light sensors are sensitive to different spectral ranges, in particular wavelengths. By way of example, a plurality of different light sensors which react sensitively to the primary light and/or to a secondary light can be arranged in groups (e.g. in pairs) in the circumferential direction around the phosphor volume. This increases further an identification or detectability of holes and cracks, for example by an evaluation of a correlation of an intensity and/or a change in intensity of spectrally different light portions in a common solid angle range. By way of example, for this purpose it is possible to evaluate or determine intensity ratios of primary light to secondary light for one or more solid angle ranges.

The at least one light sensor can be arranged tangentially or in a plane alongside the in particular layerlike phosphor volume. Alternatively or additionally, it may be arranged obliquely with respect to a plane of the in particular layerlike phosphor volume.

In yet another configuration, at least one light sensor is configured and arranged to detect light in a light path between the at least one primary light source and the phosphor volume. During normal operation, such a light path corresponds to the light path of primary light that is guided to the phosphor volume. This configuration makes use of the fact that if the phosphor volume has holes, for example, light from the at least one additional light source which is incident on the useful side of the phosphor volume can penetrate through the phosphor volume to a greater extent than without these instances of damage. With the primary light source switched off, this means that, in the case of a damaged phosphor volume, a higher luminous flux is measured in this light path than without damage or a luminous flux is even measured in the first place. A light sensor that detects said luminous flux may be a light sensor which can ascertain an intensity of the luminous flux. Said light sensor is advantageously useable for the case where the luminous flux is to be compared with a luminous flux of an undamaged phosphor volume as reference. This light sensor may also be used during normal operation to regulate a luminous flux of the primary light. A light sensor that detects said luminous flux may alternatively be a light sensor which can only ascertain the presence of the luminous flux, without ascertaining the intensity thereof or without being able to ascertain the intensity thereof with sufficient accuracy. Such a light sensor may suffice e.g. for the case where a damaged phosphor volume eventually first couples light into the light path upon irradiation by the additional light source(s).

In one configuration, the at least one additional light source radiates only primary light onto the phosphor volume, in particular if a ratio of the primary light to the secondary light generated in this case corresponds at least approximately to a ratio of the useful light during normal operation. This simplifies a construction and an evaluation. In this regard, an additional light source may correspond to a primary light source, e.g. be a laser that emits blue light. However, the additional light source may also emit (test) light of a different spectral distribution than the at least one primary light source, for example if the spectral distribution of the additional light source is more suitable for determining damage.

In one development, the at least one additional light source radiates light having a portion of primary light and a portion of at least one secondary light onto the phosphor volume. As a result, the test light can be adapted particularly accurately to the composition of the useful light emitted by the phosphor volume e.g. even if an intensity of the light emitted by the at least one additional light source does not correspond to the intensity of the useful light during normal operation. This in turn facilitates a comparability with an undamaged phosphor volume. This in turn supports a use of identical or analogous evaluation processes for determining damage in test operation (with activated additional light source(s) and deactivated primary light source(s)) and during normal operation (with deactivated additional light source(s) and activated primary light source(s)).

In one configuration, moreover, the evaluation unit is configured to determine a presence of the case of damage of the phosphor volume on the basis of at least one ratio of sensor data associated with at least one pair of different light portions. This ratio is particularly suitable for ascertaining cracks and holes. This configuration can include a comparison of the ratio with a reference value or threshold value, wherein a case of damage is ascertained for example by the threshold value being reached, exceeded or undershot. The ratio can be evaluated for a plurality of pairs of different light portions which are captured or detected e.g. by pairs of light sensors having different spectral sensitivities which are arranged in a manner spatially distributed with respect to one another.

By way of example, a ratio of the primary light and a secondary light can be evaluated or determined. If only the primary light (e.g. blue light) and one secondary light (e.g. yellow light) are generated, the ratio of the intensity of the primary light to the intensity of the secondary light (or vice versa) can be used, that is to say e.g. of the blue light to the yellow light. If the primary light (e.g. blue light), a first secondary light (e.g. yellow light) and a second secondary light (e.g. red light) are generated, in principle intensity ratios of arbitrary pairs thereof may be determined or evaluated, e.g. of the blue light to the yellow light, of the blue light to the red light and/or of the yellow light to the red light.

In another configuration, the lighting device is a module of a vehicle lighting system. At least one additional light source may then be fixed to the module. In another configuration, the lighting device is a headlight, e.g. of a vehicle lighting system. At least one additional light source may then be arranged at a reflector of the headlight, for example at an (outer) side facing away from the reflective (inner) side. The additional light source arranged on the outer side may then be directed onto the phosphor volume through a hole in the reflector. In another configuration, at least one additional light source is directed at a reflective (inner) side of the reflector of the headlight. It may be arranged outside the reflector, in particular.

Various embodiments further provide a method for determining a case of damage of a phosphor volume of a lighting device, wherein the lighting device includes: at least one primary light source for generating primary light, at least one light sensor for detecting light generated by the at least one primary light source and at least one additional light source for irradiating the phosphor volume, and wherein the method includes at least the following steps: irradiating the phosphor volume only by means of the additional light source, and determining a case of damage of the phosphor volume on the basis of sensor data of at least one light sensor. The method can be configured analogously to the lighting device and affords the same advantages.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the disclosed embodiments. In the following description, various embodiments described with reference to the following drawings, in which:

The FIGURE shows a sectional illustration in side view of a lighting device in the form of a vehicle headlight according to various embodiments.

DETAILED DESCRIPTION

The FIGURE shows a lighting device in the form of a vehicle headlight W as a sectional illustration in side view. The vehicle headlight W includes a light generating module 1 for generating useful light. The light generating module 1 includes at least one primary light source in the form of at least one laser 2 for generating here e.g. blue primary light P.

In the path of the primary light P emitted by the at least one laser 2 there is situated at a distance a reflector in the form of a deflection mirror 3, which radiates the primary light P onto a phosphor volume in the form of a phosphor lamina 4. The phosphor lamina 4 converts the primary light P partly into light having a longer wavelength, namely here into a yellow secondary light S. Blue-yellow or white mixed light P, S is generated at the useful light side facing away from the deflection mirror 3 and can be emitted as the useful light from the light generating module 1. Said mixed light P, S is further radiated onto a secondary optical unit of the vehicle headlight W, here illustrated by a reflector R, which images the mixed light P, S into a far field. In this regard, e.g. a low beam, a high beam, a fog light, a cornering light or the like can be generated by the vehicle headlight W.

In the light generating module 1, there is situated a first light sensor 5 for detecting light in the light path between the at least one laser 2 and the deflection mirror 3. For tapping off or coupling out light from said light path, a beam splitter 6, e.g. a partly transmissive mirror, is provided, which branches off a comparatively small proportion of the light passing in the light path to the first light sensor 5. The first light sensor 5 may be sensitive to visible light (including the primary light P and the secondary light S) or only to the primary light P (but not the secondary light S).

Additionally or alternatively, at least one second light sensor 7 may be present which detects the mixed light P, S generated by the phosphor lamina 4. For this purpose, a reflector 8 is provided here, which guides the mixed light P, S to the at least one second light sensor 7. In one variant, the at least one second light sensor 7 may also be able to detect or sense the light directly (that is to say without a reflector). In another variant, e.g. a plurality of pairs of light sensors 5, 7 sensitive to primary light P and/or to secondary light S are arranged in the circumferential direction around the phosphor lamina 4.

The sensor data of the first light sensor 5 and/or of the second light sensor 7 can be evaluated by means of an evaluation unit 9. The evaluation unit 9 is configured in particular for determining a case of damage of the phosphor lamina 4 on the basis of the sensor data.

In order to determine a case of damage of the phosphor lamina 4 in a test phase outside normal operation, that is to say with the laser 2 switched off, the vehicle headlight W includes at least one additional light source Z1, Z2, Z3 for irradiating the useful light side of the phosphor lamina 4, in particular with primary light P. The at least one additional light source Z1, Z2, Z3, at least one light sensor 5, 7 and the evaluation unit 9 are operated in the test phase. A first additional light source Z1 is fitted to the light generating module 1, a second additional light source Z2 is fitted to an outer side of the reflector R and/or a third additional light source Z3 is fitted outside the reflector R in its light path. The second additional light source Z2 may radiate e.g. through a hole (not illustrated) in the reflector R. In order to keep down costs and complexity, only one of said additional light sources Z1, Z2, Z3 may be present.

With the primary light P being radiated onto the phosphor lamina 4 by means of the at least one additional light source Z1, Z2, Z3, mixed light P, S is again generated there, said mixed light being detectable by the at least one second light sensor 7. Since the primary light P is radiated onto the useful light side of the phosphor lamina 4, it does not emerge, or emerges only to a small extent (e.g. as a result of scattering), from the vehicle headlight W. A more intensive primary light portion passing through the phosphor lamina 4 if appropriate on account of holes and/or cracks is rather radiated into the light generating module 1.

The evaluation unit 9 may be configured for example to determine a presence of mechanical damage of the phosphor lamina 4 (e.g. as a result of holes and/or cracks) on the basis of at least one ratio of primary light P to secondary light S which have been radiated into an at least approximately identical solid angle range. This can take place e.g. by an evaluation of the sensor data of at least one pair of light sensors 5, 7 sensitive to primary light P and/or secondary light S. In this case, with a plurality of such pairs, a correlation of different ratios of a plurality of pairs can also be used. The case of damage may be determined for example by a comparison with a ratio of a non-damaged phosphor lamina 4 as reference.

The case of damage can additionally or alternatively be determined by virtue of the fact that the first light sensor 5 detects a light signal from the light path between the at least one primary light source and the deflection mirror 3. Said light signal may be generated e.g. on the basis of primary light P which penetrates through the phosphor lamina 4 owing to a hole or the like and is coupled into said light path by the deflection mirror 3. If appropriate, secondary light S may also be coupled in. The case of damage may be assumed to be present for example if the first light sensor 5 receives a light signal which is significantly more intense than a reference value in the case of a non-damaged phosphor lamina 4.

While the disclosed embodiments have been particularly shown and described with reference to specific embodiments, it should be understood by those skilled in the art that various changes in form and detail may be made therein without departing from the spirit and scope of the disclosed embodiments as defined by the appended claims. The scope of the disclosed embodiments is thus indicated by the appended claims and all changes which come within the meaning and range of equivalency of the claims are therefore intended to be embraced.

Generally, "a(n)", "one" etc. can be understood to mean a singular or a plural, in particular in the sense of "at least one" or "one or a plurality" etc., as long as this is not explicitly excluded, e.g. by the expression "exactly one", etc.

Moreover, a numerical indication can encompass exactly the indicated number and also a customary tolerance range, as long as this is not explicitly excluded.

The invention claimed is:

1. A lighting device, comprising:
   at least one primary light source for generating primary light,
   a phosphor volume spaced apart from the at least one primary light source and serving for at least partly converting the primary light into secondary light having a different wavelength,
   at least one light sensor for detecting light generated by the at least one primary light source, and
   an evaluation unit for determining a case of damage of the phosphor volume on the basis of sensor data of at least one light sensor, wherein the lighting device
   comprises at least one additional light source for irradiating the phosphor volume and
   is designed to operate the at least one additional light source, the at least one light sensor and the evaluation unit with the primary light source switched off.

2. The lighting device as claimed in claim 1, wherein at least one light sensor is configured and arranged to detect light emitted by the phosphor volume.

3. The lighting device as claimed in claim 2, wherein a plurality of light sensors are arranged in the circumferential direction around the phosphor volume.

4. The lighting device as claimed in claim 1, wherein at least one light sensor is configured and arranged to detect light in a light path between the at least one primary light source and the phosphor volume.

5. The lighting device as claimed in claim 1, wherein the at least one additional light source radiates primary light onto the phosphor volume.

6. The lighting device as claimed in claim 1, wherein the evaluation unit is configured to determine a presence of the case of damage of the phosphor volume on the basis of at least one ratio of sensor data associated with at least one pair of different light portions.

7. The lighting device as claimed in claim 1, wherein the at least one additional light source is configured to radiate its light onto a useful light side of the phosphor volume.

8. The lighting device as claimed in claim 1, wherein the lighting device is a module of a vehicle lighting system.

9. The lighting device as claimed in claim 1, wherein the lighting device is a headlight.

10. A method for determining a case of damage of a phosphor volume of a lighting device, wherein the lighting device comprises:

at least one primary light source for generating primary light, at least one light sensor for detecting light generated by means of the at least one primary light source, and at least one additional light source for irradiating the phosphor volume, the method comprising:

irradiating the phosphor volume only by means of the additional light source, and determining a case of damage of the phosphor volume on the basis of sensor data of at least one light sensor.

* * * * *